United States Patent
Duthilleul

(10) Patent No.: US 9,642,293 B2
(45) Date of Patent: May 2, 2017

(54) MULTILAYER CASING DEVICE FOR ATTENUATING ELECTROMAGNETIC WAVES

(71) Applicant: Pascal Duthilleul, Ganges (FR)

(72) Inventor: Pascal Duthilleul, Ganges (FR)

(*) Notice: Subject to any disclaimer, the term of this patent is extended or adjusted under 35 U.S.C. 154(b) by 461 days.

(21) Appl. No.: 14/373,242

(22) PCT Filed: Jan. 17, 2013

(86) PCT No.: PCT/FR2013/050107
§ 371 (c)(1),
(2) Date: Jul. 31, 2014

(87) PCT Pub. No.: WO2013/114019
PCT Pub. Date: Aug. 8, 2013

(65) Prior Publication Data
US 2014/0368061 A1  Dec. 18, 2014

(30) Foreign Application Priority Data

Feb. 1, 2012 (FR) ..................... 12 50943

(51) Int. Cl.
*H05K 9/00* (2006.01)
*A61N 1/16* (2006.01)
(Continued)

(52) U.S. Cl.
CPC ............ *H05K 9/0088* (2013.01); *A61N 1/16* (2013.01); *H01Q 1/245* (2013.01); *H01Q 1/526* (2013.01); *H01Q 17/00* (2013.01); *H04B 1/3838* (2013.01); *H05K 9/006* (2013.01); *H05K 9/0043* (2013.01); *H05K 9/0049* (2013.01); *H05K 9/0056* (2013.01)

(58) Field of Classification Search
CPC ......................................................... H05K 9/00
USPC ........................................................ 361/818
See application file for complete search history.

(56) References Cited

U.S. PATENT DOCUMENTS 5,083,112 A * 1/1992 Piotrowski ......... G08B 13/2408
340/551
5,925,455 A * 7/1999 Bruzzone ........... B65D 81/3446
252/518.1

(Continued)

FOREIGN PATENT DOCUMENTS

EP 0915572 A1 5/1999
EP 1174162 A1 1/2002

(Continued)

*Primary Examiner* — Adi Amrany
(74) *Attorney, Agent, or Firm* — IM IP Law; C. Andrew Im

(57) ABSTRACT

A multilayer casing device for attenuating electromagnetic waves is made of at least one textile material, at least one metal material. The device is made up of a stack provided with at least, consecutively from the inside to the outside: a first diamagnetic metal material layer at least partially made of copper, a second textile layer at least partially made of wool or cotton, a third layer made of a ferromagnetic material, and a fourth textile layer at least partially made of wool and cotton. The device is also made up of a complementary stack of identical layers (the second textile layer, the third ferromagnetic layer and the fourth textile layer) extending symmetrically in relation to the first copper layer.

5 Claims, 1 Drawing Sheet

(51) Int. Cl.
    *H01Q 1/24*     (2006.01)
    *H01Q 1/52*     (2006.01)
    *H01Q 17/00*     (2006.01)
    *H04B 1/3827*     (2015.01)

(56) References Cited

U.S. PATENT DOCUMENTS

| | | | | |
|---|---|---|---|---|
| 7,176,387 | B1* | 2/2007 | Huang | D02G 3/12 |
| | | | | 174/393 |
| 8,937,816 | B2* | 1/2015 | Trombino | A45C 11/00 |
| | | | | 174/384 |
| 9,049,777 | B2* | 6/2015 | Beach | H01B 1/22 |
| 2003/0223213 | A1* | 12/2003 | Daoud | H05K 9/0026 |
| | | | | 361/818 |
| 2004/0020674 | A1* | 2/2004 | McFadden | H05K 9/0088 |
| | | | | 174/394 |
| 2005/0276978 | A1* | 12/2005 | Chen | B82Y 10/00 |
| | | | | 428/408 |
| 2009/0002968 | A1* | 1/2009 | Li | A61B 6/06 |
| | | | | 361/818 |
| 2010/0186155 | A1* | 7/2010 | Maner | A41D 1/20 |
| | | | | 2/466 |
| 2012/0236528 | A1* | 9/2012 | Le | H05K 9/0088 |
| | | | | 361/818 |

FOREIGN PATENT DOCUMENTS

| | | | |
|---|---|---|---|
| EP | 1981324 A1 | | 10/2008 |
| JP | 2001 217590 A | | 8/2001 |
| JP | 2005002532 A | * | 1/2005 |
| WO | 2008 044414 A1 | | 4/2008 |

\* cited by examiner

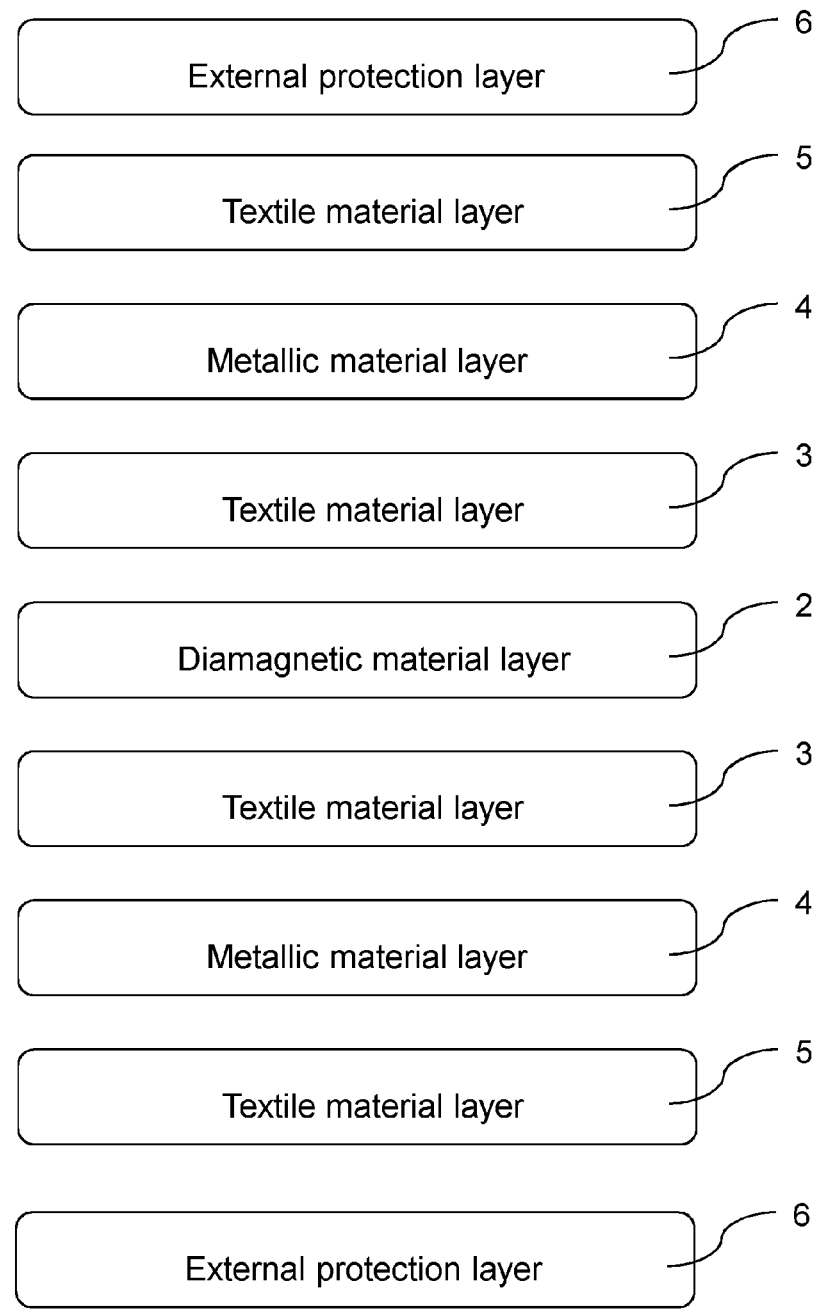

MULTILAYER CASING DEVICE FOR ATTENUATING ELECTROMAGNETIC WAVES

RELATED APPLICATIONS

This application is a § 371 application from PCT/FR2013/050107 filed Jan. 17, 2013, which claims priority from French Patent Application No. 12 50943 filed Feb. 1, 2012, each of which is herein incorporated by reference in its entirety.

TECHNICAL FIELD OF THE INVENTION

The present invention belongs to the field of electromagnetism and more specifically of protection from electromagnetic waves.

The invention concerns particularly a multilayer casing device for attenuating electromagnetic waves.

Such a device will find a preferred application, but in a non-limiting manner, in attenuating radiation emitted by mobile terminals, notably of cellular telephone type. In order to achieve this, the multilayer casing device according to the invention is in the form of a flexible or semi-rigid material and can be shaped into a pouch, within which said terminal is placed and is then surrounded by this casing.

BACKGROUND OF THE INVENTION

Currently, many technologies in everyday use utilize radio frequencies to emit and receive information. These technologies then generate an electromagnetic field which, in proximity to a living being, is likely to interfere with the biological operations, in particular of the nervous system.

Several symptoms have been frequently observed in people exposed repeatedly to an electromagnetic field, namely headaches, increased stress, nervousness and irritability, sleep problems, increased tiredness, as well as weakened immune defenses, problems with concentration and memory, problems with the neuroendocrine-immune system and some fields could be the source of increased risks of cancer and miscarriage.

In this context, cellular telephones called "mobile" or "portable" are radiofrequency transmitters operating at frequencies of between 450 and 2700 MHz with a maximum power emission of between 0.1 and 2 Watts. Even though such transmitters are low-power types, the duration of their users' exposure exceeds several hours per day, but the influence may be increased because of their close proximity in use, in contact with the ear during telephone conversations or carried on the person, in a pocket, for the remainder of the time.

Given this, it is necessary to limit a user's exposure to the electromagnetic fields generated by a terminal, without this degrading the latter's operating conditions.

One solution is envisaged in document EP 1 981 324, describing a cellular telephone pouch made of a material that creates a barrier to protect the telephone from any radiation or emission. Said material is made of several layers formed from a weave of warp and weft threads, where one or the other is made of an electrically conductive compound, in particular metal in ribbon form such as brass, nickel or copper. However, such a shell blocks the electromagnetic radiation completely, both from and towards the telephone, which can then remain switched on but will be disconnected from the network's electromagnetic field and the other electromagnetic fields.

Another solution consists of a semi-rigid protective shell that limits the radiation of the electromagnetic fields coming from a cellular telephone. As described in document EP 0 915 572, said shell is made of elastomeric material, covered in or including a metal lattice or mesh, such as polyester covered in copper and nickel. Such a shell is not entirely satisfactory, however, as it only covers part of the telephone, limiting the electromagnetic radiation only at the location of the radio frequency emission and reception antenna.

An alternative solution consists of a textile for attenuating the electromagnetic radiation. As described in document WO 2002/05892, such a textile is made from textile fibers and at least one electromagnetic field attenuation compound, contained in the textile in a 5 to 15% proportion within said textile. In particular, the latter is made of woven fibers with which said attenuation compound is woven or incorporated, which may be firstly metallic, such as silver, gold, platinum or copper, or secondly a crystalline structure type of semiconductor containing in particular silicone, selenium, germanium or boron. In this way, by weaving it with a natural fiber such as wool or cotton or with a synthetic fiber such as polyester or acrylic, it is possible to manufacture a textile with a view to producing an item of clothing or a portion of an item of clothing, such as a pocket, through which electromagnetic radiation is limited.

However, a disadvantage of such a textile lies in the fact that it is complicated and costly to manufacture, utilizing costly materials. Moreover, the item of clothing blocks the radiation, disconnecting the telephone from the network.

Another solution from a related field is described in document WO 2008/044414 and concerns an apron for protecting from electromagnetic fields. In particular, such an apron is made of a multilayer structure, which gives it its ability to completely block the electromagnetic waves. In effect, the structure of such an apron constitutes a shield that the waves of an electromagnetic field cannot penetrate.

Such a shield is preferably designed to be used as protective clothing, in particular for persons who have a pacemaker, the operation of which is likely to be disrupted by an electromagnetic field. In this way, this apron makes it possible to block the radio waves and the electromagnetic fields, in particular coming from induction cooktops.

More specifically, the front and rear faces of its structure are covered in layers made of a woven synthetic or natural fiber material, notably, as an example, wool or cotton. It can be seen that the only purpose of these textile layers is to provide cover layers in front of and behind the apron, improving the finish so that the apron looks like an item of clothing. They are not arranged so as to play a part between the other layers.

Moreover, said structure is made of a copper absorption layer and of an aluminum blocking layer or "shielding sheet". In addition, the copper layer may be in the form of a sheet, lined with iron or nickel, between 10 and 35 microns thick. Preferably, the 35-micron thickness provides sufficient shielding to absorb the magnetic field, while retaining a flexible characteristic of the garment. The role of this copper layer is therefore to absorb the magnetism from the electromagnetic field.

In addition, the aluminum layer acts as a reflector, using this material's characteristic of impermeability to electromagnetic radiation. It cuts the electromagnetic field that has not been absorbed by the copper layer.

Generally, the copper layer attenuates the electromagnetic field and the aluminum layer blocks the field thus attenuated. It should be noted that the copper and aluminum layers are separated by carbon sheets. These carbon sheets are obtained by polymerization so as to constitute a flexible and uniformly compact multilayer structure with the copper and aluminum layers; the cloth layers are in no way involved.

Thus, the structure of this device makes it possible to block electromagnetic fields with frequencies between 20 kHz and 2 Gigahertz (GHz), thanks to an aluminum layer for completely blocking the electromagnetic field. However, this device does not make it possible to simply reduce the electromagnetic field so as to provide for the operation of an electronic device, in particular a cellular telephone.

OBJECT AND SUMMARY OF THE INVENTION

The aim of the present invention is to overcome the disadvantages of the state of the art by proposing a multi-layer casing device for attenuating electromagnetic waves.

In particular, said device is made of at least one textile material and at least one metallic material, characterized in that it is made of a superimposition provided with at least, successively from the inside to the outside, a first layer made of metallic diamagnetic material made at least in part of copper, a textile second layer at least partly in wool or cotton, a third layer made of a ferromagnetic material, a textile fourth layer at least partly in wool or cotton, and in that it is made of an additional superimposition of identical layers extending symmetrically in relation to said first copper layer.

Through its symmetrical superimposition of layers, around a metal core, such a casing provides a synergy that makes it possible to channel the electromagnetic radiation, in particular emitted from the telephone, towards said core. The latter only captures a portion of this radiation to transform it, letting an attenuated radiation, sufficient to connect said telephone to the communications network, filter through. In particular, the superimposition according to the invention makes it possible to create a Casimir effect making it possible to alter the electromagnetic radiation by transforming it into photons.

Moreover, according to other characteristics, said third layer may be metallic and made at least in part of steel wool.

According to a preferred embodiment, said device comprises at least one peripheral protection layer.

According to another embodiment, said layers are fastened together, stitched at least at their perimeter. In this way, the invention makes it possible to attenuate the waves emitted by the telephone. Tests have shown a reduction of the SAR ("Specific Absorption Rate") in Watt per kilogram (W/kg) of over 90% when a telephone is fitted with a device according to the invention.

Other measurements have made it possible to measure an attenuation of emitted power in milliwatts (mW) of over 70% on average for a telephone fitted with said device, i.e. about 10 mW of absorption by the device on average.

BRIEF DESCRIPTION OF THE DRAWINGS

Other features and advantages of the invention will become apparent in the following description of non-limiting embodiments of the invention with reference to the appended FIGURE that represents schematically the superimposition of different layers according to a preferred embodiment of said casing device.

DETAILED DESCRIPTION OF THE EMBODIMENTS

The present invention concerns particularly a multilayer casing device 1 for attenuating electromagnetic waves.

Such a device 1 is made of at least one textile material and at least one metallic material. More specifically the invention consists of a synergy of the actions of several layers made of metallic and textile materials, placed in adjacent manner.

Advantageously, said device 1 is made of a superimposition provided with at least, successively from the inside to the outside, a first layer 2 made of preferably metallic diamagnetic material, a textile second layer 3 exhibiting dipolar electrostatic characteristics, a third layer 4 made of preferably metallic ferromagnetic material, a textile fourth layer 5 exhibiting dipolar electrostatic characteristics.

More specifically, said diamagnetic first layer 2 is metallic and made at least partly of copper, the textile second layer 3 is made at least partly of wool or cotton, the ferromagnetic and metallic third layer 4 is at least partly made of steel wool, whereas the textile fourth layer 5 is at least partly made of wool or cotton.

According to the preferred embodiment, said first layer 2 is made from one sheet of copper or a copper-plated sheet or one mostly made of copper. This sheet may have several thicknesses, in particular of the order of a millimeter.

Moreover, the textile second 3 and fourth 5 layers can be identical, made of a woven material of natural fibers of wool or cotton or of a mixture of both. The function of these two types of textile is to provide an insulating layer between the copper and the steel as well as between the steel and the outside. Thus, a layer with dipolar electrostatic properties is created, which generates a different field when the electromagnetic radiation goes through it.

Moreover, said third layer 4 can be made of a steel wool fibrous mat, whose thickness can vary, in particular of the order of one millimeter. In addition, said steel wool's grade can vary: nos. 0000, 0 or 5. This layer 4 provides a Casimir effect, altering the electromagnetic field to transform it at least in part into photons. In addition, this Casimir effect is amplified through to the core of the casing 1 constituted by the central copper layer.

According to the preferred embodiment, shown in the FIGURE, said casing device 1 can be made of a complementary superimposition of identical layers extending symmetrically in relation to said first copper layer 2. In effect, the copper acts as the central core of the casing 1 and layers made of identical material alternate symmetrically on either side, namely the second layer 3 made of wool or cotton, the third layer 4 made of steel wool and the fourth layer 5 made of wool or cotton.

It should be noted that even though the layers are identical, the thickness and composition of the layers may vary. In addition, said second layer 3 or third layer 4 on one side can be made of wool, while it is made of cotton on the other side, or vice-versa.

Advantageously, this particular combination of said superimposed layers 2, 3, 4, 5 generates an effect channeling the electromagnetic radiation towards the first copper layer 2, which then acts as the receiving core at the center of the material, the radiation then converges towards the copper sheet.

Furthermore, the alternating conducting and insulating layers provide an effect of absorption by the ferromagnetic layers 4 and an effect of transformation of the electromagnetic radiation into photons at the location of the copper layer 2, the latter, being diamagnetic, is therefore insensitive to magnetic fields.

According to the same preferred embodiment, said device 1 may comprise at least one peripheral protection layer 6. The latter can be made of a coating layer 6 made of an inert material, with no influence when an electromagnetic field goes through it. It then only acts as a coating, as an esthetic and protective covering.

According to an embodiment, said peripheral layer 6 can be made of natural or synthetic leather.

In order to make the casing device 1 conform to its use, said layers 2, 3, 4, 5, 6 are fastened together, in particular stitched at least at their perimeter.

It should be noted that the layers 2, 3, 4, 5, 6 adjoin each other, with no space between them.

Furthermore, in the preferred case of use as a cellular telephone shell or pouch, the casing 1 according to the invention can be cut and stitched according to the dimensions of said telephone. In addition, support flaps or straps can be added to fasten the telephone to its shell.

According to other uses, said device 1 can be conformed to adapt to other terminals, in particular computers, tablets, microwaves, etc.

In this way, the casing device 1 according to the invention makes it possible to attenuate the radiation emitted by a terminal, in particular a cellular telephone, without this completely blocking the electromagnetic field, ensuring the connection of the apparatus to its communications network.

Furthermore, the invention is designed to be simple for large-scale manufacturing, with low cost materials keeping manufacturing costs low.

The invention claimed is:

1. A multilayer casing device for attenuating electromagnetic waves, made of at least one textile material and of at least one metallic material, comprising a superimposition provided with at least, successively:
    a textile first layer at least partly in wool or cotton;
    a second layer made of a ferromagnetic material;
    a textile third layer at least partly in wool or cotton;
    a fourth layer made of metallic diamagnetic material made at least in part of copper;
    a textile fifth layer at least partly in wool or cotton;
    a sixth layer made of a ferromagnetic material; and
    a textile seventh layer at least partly in wool or cotton.

2. The casing device according to claim 1, wherein said second layer is metallic and made at least in part of steel wool.

3. The casing device according to claim 2, further comprising at least one peripheral protection layer.

4. The casing device according to claim 3, wherein all layers are fastened together, stitched at least at their perimeter.

5. The casing device according to claim 1, further comprising at least one peripheral protection layer.

* * * * *